(12) United States Patent
Iwata et al.

(10) Patent No.: US 11,291,365 B2
(45) Date of Patent: Apr. 5, 2022

(54) OCT SYSTEM AND REFERENCE ATTACHMENT

(71) Applicant: NIDEK CO., LTD., Aichi (JP)

(72) Inventors: Shinya Iwata, Aichi (JP); Kenji Aoki, Aichi (JP); Takuya Matsumoto, Aichi (JP)

(73) Assignee: NTDEK CO., LTD., Aichi (JP)

( * ) Notice: Subject to any disclaimer, the term of this patent is extended or adjusted under 35 U.S.C. 154(b) by 268 days.

(21) Appl. No.: 16/778,074

(22) Filed: Jan. 31, 2020

(65) Prior Publication Data
US 2020/0245863 A1    Aug. 6, 2020

(30) Foreign Application Priority Data
Feb. 1, 2019   (JP) .............................. JP2019-017515

(51) Int. Cl.
*A61B 3/10*   (2006.01)

(52) U.S. Cl.
CPC ................... *A61B 3/102* (2013.01)

(58) Field of Classification Search
CPC ............. A61B 3/102; G01B 9/02015; G01B 9/02028; G01B 9/02044; G01B 9/02091
USPC ........................................................... 351/205
See application file for complete search history.

(56) References Cited

U.S. PATENT DOCUMENTS

| 6,233,370 B1* | 5/2001 | Fujino | G01B 9/0201 385/11 |
| 2013/0250237 A1* | 9/2013 | Ueno | G01B 9/02089 351/206 |
| 2016/0038023 A1* | 2/2016 | Endo | A61B 3/102 351/206 |

FOREIGN PATENT DOCUMENTS

| EP | 2 901 919 A1 | 8/2015 |
| JP | 2015-43844 A | 3/2015 |
| JP | 2016-123467 A | 7/2016 |

* cited by examiner

*Primary Examiner* — Mohammed A Hasan
(74) *Attorney, Agent, or Firm* — Sughrue Mion, PLLC

(57) ABSTRACT

An OCT system includes an OCT optical system and a reference attachment. The OCT optical system has a beam splitter for splitting light into a measurement optical path and a reference optical path, a photodetector, a first waveguide, a second waveguide, and first connectors provided at end portions of the first waveguide and the second waveguide respectively for indirectly or directly connecting the first waveguide and the second waveguide. The reference attachment has a third waveguide, and second connectors formed at both ends of the third wave guide and configured to be attachable to and detachable from the first connector, and is attached to and detached from the OCT optical system h attaching and detaching each of the second connectors to and from the first connector to change an optical path length of the reference optical path.

8 Claims, 7 Drawing Sheets

FUNDUS PERIPHERAL AREA

FUNDUS CENTER AREA

FUNDUS PERIPHERAL AREA 200b (or 210b)
203 (or 212)
203 (or 216)
100b
131, 205 (or 217)
108, 201 (or 211)

OCT SYSTEM AND REFERENCE ATTACHMENT

CROSS-REFERENCE TO RELATED APPLICATIONS

This application is based on and claims priority under 35 USC 119 from Japanese Patent Application No. 2019-017515 filed on Feb. 1, 2019, the contents of which are incorporated herein by reference.

TECHNICAL FIELD

The present disclosure relates to an OCT system and a reference attachment.

BACKGROUND

An OCT apparatus processes, for example, a spectral interference signal between measurement light and reference light output from an OCT optical system to obtain OCT data of a subject eye. For example, in a case where a fundus of the subject eye is imaged, an individual difference exists in a distance from an exit window of the measurement light to the fundus, and thereby, an optical path length difference between the measurement light and the reference light may vary for each subject eye. Therefore, an apparatus provided with an optical member which is driven to correct the optical path length difference between the measurement light and the reference light is known in related art (see JP-A-2015-43844).

Further, JP-A-2016-123467 discloses an apparatus in which an imaging range on a fundus is changed by attaching or detaching an attachment between a main body of the apparatus and a subject eye.

For example, a case where the amount of change in an optical path length difference due to attachment/detachment of an attachment is greater in each stage than the amount of change in an optical path length difference due to an individual difference of a subject eye. As a result of study by the present inventor, a device of related art does not sufficiently correct a change in the optical path length difference due to the attachment/detachment of the attachment. Further, it is not assumed at all that an imaging range not assumed at the beginning can be imaged afterwards by using an attachment or the like.

Further, a case where the attachment or the like is optionally provided to a user is considered. In this case, it is not necessary that a member for correcting an optical path length difference corresponding to attachment/detachment of an attachment is previously incorporated in an OCT apparatus of the user who does not need the attachment. Meanwhile, there is a user who does not need the attachment at the beginning but wants the attachment afterwards.

SUMMARY

In view of the problems of related art, a technical object of this disclosure is to provide an OCT system and a reference attachment in which it is easy to expand or change an imaging range.

(1) There is provided an OCT system including:

an OCT optical system including a beam splitter for splitting light from an OCT light source into a measurement optical path and a reference optical path, a photodetector for detecting a spectral interference signal between measurement light guided onto tissue of a subject eye via the measurement optical path and reference light from the reference optical path, a first waveguide forming apart of the reference optical path, and a second waveguide forming a part of the reference optical path; and a reference attachment, in which the OCT optical system includes first connectors, provided at an end portion of the first waveguide and at an end portion of the second waveguide respectively, for indirectly or directly connecting the first waveguide and the second waveguide, in which the reference attachment includes a third waveguide, and second connectors formed at both ends of the third waveguide and configured to be attachable to and detachable from the first connector, and in which the reference attachment is attached to and detached from the OCT optical system by attaching and detaching each of the second connectors to and from the first connector to change an optical path length of the reference optical path.

(2) in the OCT system according to the above (1), in the reference optical path, the first waveguide is formed on a side of the beam splitter, and the second waveguide is formed on the photodetector side with respect to the first waveguide.

(3) In the OCT system according to the above (1), a first attachment being the reference attachment attached to the OCT optical system is replaced with a second attachment being the reference attachment having a different optical path length of the third waveguide from the first attachment to change the optical path length of the reference optical path.

(4) In the OCT system according to the above (1), a change in the optical path length of the reference light caused by attaching and detaching the reference attachment corresponds to a change in the optical path length by inserting and removing a third attachment on the measurement optical path.

(5) In the OCT system according to the above (1), the reference attachment includes a device that controls to vary an optical path length of the third waveguide.

(6) There is provided a reference attachment configured to be attached to and detached from an OCT optical system including:

the OCT optical system includes, a beam splitter for splitting light from an OCT light source into a measurement optical path and a reference optical path, a photodetector for detecting a spectral interference signal between measurement light guided onto tissue of a subject eye via the measurement optical path and reference light from the reference optical path, a first waveguide which forms a part of the reference optical path and is on the beam splitter side, and a second waveguide which forms a part of the reference optical path and is on the photodetector side with respect to the first waveguide, and in which the reference attachment includes a third waveguide and is configured to be attachable to and detachable from the OCT optical system such that the third waveguide is inserted and removed between an end portion of the first waveguide and an end portion of the second waveguide.

(7) In the reference attachment according to the above (6), the third waveguide is diverged to at least two of a first divergence optical path and a second divergence optical path having different optical path lengths, and reference light passing through the first divergence optical path and reference light passing through the second divergence optical path are guided to the detector simultaneously or selectively.

(8) In the reference attachment according to the above (7), the reference attachment includes a device that controls to vary an optical path length of the third waveguide.

DETAILED DESCRIPTION

An example of an embodiment of this disclosure will be described with reference to the figures. FIGS. 1 to 9B are diagrams according to examples of the present embodiment. The following chapters classified by < > are used individually or in association with each other.
<Schematic Configuration of OCT Apparatus (OCT System)>

Figure 1:
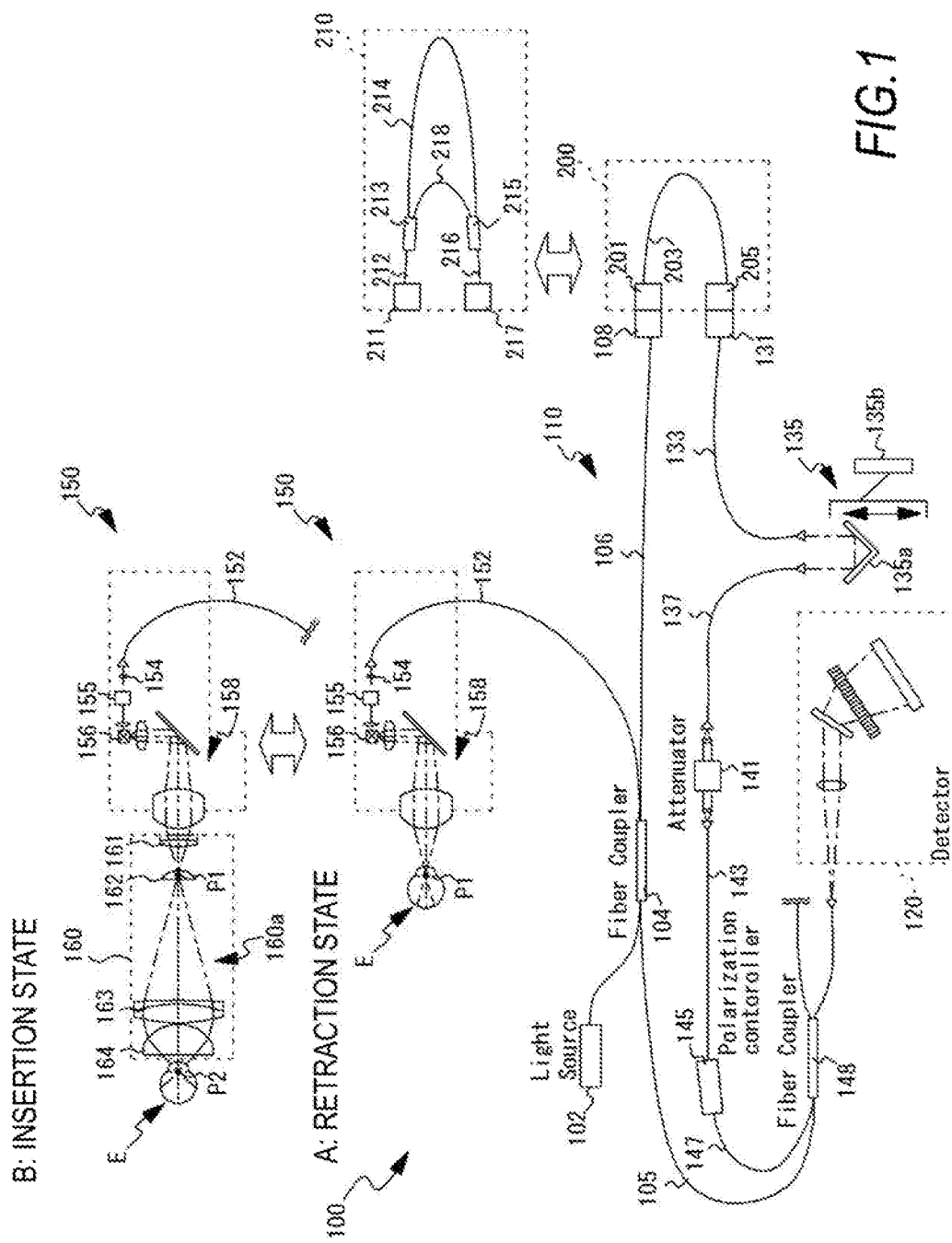
FIG. 1 is a diagram illustrating a schematic configuration of an optical system according to a first example.

An OCT apparatus (OCT system) according to the present embodiment includes an OCT optical system (for example, see FIG. 1). Further, the OCT apparatus may be capable of processing a spectral interference signal output from a detector of the OCT optical system to obtain OCT data. In this case, the OCT optical system may be, for example, a Fourier domain OCT optical system (SS-OCT optical system, SD-OCT optical system), and the OCT optical system may include a beam splitter and a photodetector. The beam splitter splits light from an OCT light source into a measurement optical path and a reference optical path. The phot detector detects a spectral interference signal between measurement light guided to a subject eye via the measurement optical path and reference light from the reference optical path. Further, the OCT apparatus may include an image processor, and the image processor may be capable of processing the spectral interference a signal output from the OCT optical system to obtain OCT data.

In the following examples, unless otherwise specified, it is assumed that a reference optical system in the OCT optical system is a transmission type. However, the present disclosure is also applicable to the OCT optical system including a reflection-type reference optical system.

<Measurement Optical Path>

The OCT apparatus may be capable of changing an irradiation condition of measurement light relating to the imaging range with a change in optical path length of the measurement optical path. The imaging range is changed by changing the irradiation condition of the measurement light relating to the imagine range and further adjusting an optical path length difference between the measurement light and the reference light as appropriate. In this case, for example, the imaging range may be changed in a depth direction or in a transverse direction. In a case where changing is made in the depth direction, the imaging range may be changed between an anterior portion of a subject eye and a fundus. Further, the changing may be made between a region on a cornea side of the anterior portion and a region on a lens side. In a case where changing is made in the transverse direction, for example, the changing may be made between a central region of the fundus and a wide-angle region of the fundus. The wide-anele region is a region including a peripheral region of the fundus around a central region (see FIG. 4). The wide-angle region may be a region including the central region in addition to the peripheral region. The irradiation condition relating to the imaging range may be, for example, a condition relating to any one of a light collecting position of the measurement light and a scanning range. In the following description, there is a case where a size of the scanning range of the measurement light in the OCT apparatus is referred to as an angle of view.

The OCT apparatus may have a light guide optical system. The irradiation condition may be switched by switching a state of the light guide optical system. The light guide optical system is formed on the measurement optical path. The light guide optical system may include at least an optical scanning unit (optical scanner) and a focus adjustment unit. Further, the light guide optical system may further include an object optical system. The light guide optical system deflects measurement light from the beam splitter by using the optical scanning unit, thereby, capable of changing a position, which is irradiated with the measurement light, on a tissue of the subject eye. Thereby, the measurement light can be scanned on the tissue.

As an example of a case where the irradiation condition of the measurement light is switched with a change in the optical path length of the measurement optical path, a case where an optical system for changing the imaging range is inserted or removed between the subject eye and an object optical system is considered. As another example, a case where a partial arrangement of the light guide optical system is changed to change the imaging range is considered.
<Reference Optical Path>

The OCT optical system of the present embodiment includes a first waveguide and a second waveguide. The first waveguide and the second waveguide both form a part of the reference optical path. The first waveguide is formed on the beam splitter side. The second waveguide is formed on the photodetector side with respect to the first waveguide. Each of the first waveguide and the second waveguide may be formed by, for example, an optical fiber or may be formed by another member or a medium.

In the present embodiment, an end portion of the first waveguide opposite to the beam splitter and an end portion of the second waveguide opposite to the photodetector may be connectable directly or indirectly to the first waveguide and the second waveguide. The two end portions are directly connected by coming into contact with one point. Further, a third waveguide (details will be described below) interposed between the two end portions, thereby indirectly connecting the two end portions. For example, the OCT optical system according to the present embodiment can change a total length of the reference optical path according to an optical path length (or presence or absence of the third waveguide) of the third waveguide interposed between the first waveguide and the second waveguide.

Incidentally, an ophthalmic OCT apparatus of related art is known which includes a device for variably controlling an optical path length, such as an optical delay line (ODL), on a reference optical path or a measurement optical path. However, this type of device is used to correct an error of the optical path length error due to an individual difference of the subject eye. Therefore, in the related art, only a device capable of varying the optical path length within a range in which the individual difference of the subject eye can be corrected has been adopted. The range that can be varied is only several mm to several tens mm at most. That is, the optical path length of the reference optical path could not be changed significantly.

In contrast to this, in the present embodiment, the total length of the reference optical path can be changed more greatly than an adjustment range by the ODL of the device of related art, according to the optical path length (or the presence or absence of the third waveguide) of the third waveguide interposed between the first waveguide and the second waveguide.

An optical connector may be provided at each of the end portions of the first waveguide and the second waveguide. Examples of the optical connector include an FC connector, an SC connector, and the like. However, the optical connector may be any member that connects the waveguides and fixes a connection relationship and is not necessarily limited to these members. In a case where two optical connectors are connected to each other, an adapter may be interposed therebetween.

<Reference Attachment>

The reference attachment includes at least the third waveguide (see, for example, FIGS. 1, 6 to 9B). The third waveguide may be placed between the first waveguide and the second waveguide to connect both. The third waveguide is connected to the first waveguide and the second waveguide to become a part of the reference optical path in the OCT optical system. A part or all of the third waveguide may be formed by, for example, an optical fiber or may be formed by another member or a medium.

In a case where an optical connector is provided at each end portion of the first waveguide and the second waveguide, the second connector detachable from the first connector may be provided at each end portion of the third waveguide, By using the optical connector, the third waveguide, the first waveguide, and the second waveguide are easily and reliably connected. Further, attachment and detachment work of the reference attachment is easily performed.

In a case where the reference attachment is attached to the OCT optical system, it is preferable that the reference attachment is fixed to the OCT optical system by a fixing portion. The fixing portion may be included in at least one of the OCT optical system and the reference attachment or may be separate from both. In a case where the OCT optical system and the reference attachment each have the first connector and the second connector as described above, the optical connectors can also serve as the fixing portions.

The reference attachment may include a case that houses the third waveguide. In this case, the end portion of the third waveguide may be exposed outside the case.

<Third Waveguide with Divergence>

The third waveguide may be diverged to at least two of a first divergence optical path and a second divergence optical path. An optical path length of the first divergence optical path is different from an optical path length of the second divergence optical path. Further, in a state where the third waveguide is connected to the first waveguide and the second waveguide, reference light passing through the first divergence optical path and reference light passing through the second divergence optical path may be guided to the detector simultaneously or selectively.

Here, in a case where the reference light passing through the first divergence optical path and the reference light passing through the second divergence optical path are simultaneously guided to the detector, it is considered that two types of spectral interference signals are simultaneously detected by the detector. For the sake of convenience, the two types of spectral interference signals are referred to as a first interference signal and a second interference signal, respectively. The first interference signal is an interference signal due to the reference light passing through the first divergence optical path. The second interference signal is an interference signal due to the reference light passing through the second divergence optical path. At this time, it is considered that the reference light passing through the first divergence optical path and the reference light passing through the second divergence optical path can each obtain a sufficient amount of light to obtain the interference signal. Originally, the reference light is obtained by subtracting measurement light from light from an OCT light source. A subject eye is on a measurement optical path as an element that greatly attenuates the amount of light. However, there is no need for the element that greatly attenuates the amount of light on the reference optical path. Therefore, even if the reference light is simultaneously guided to the first divergence optical path and the second divergence optical path, each of the light passing through the first divergence optical path and the light passing through the second divergence optical path has a sufficient amount of light to obtain an interference signal with the measurement light. In this case, since the first divergence optical path and the second divergence optical path have different optical path lengths, it is possible to simultaneously obtain, for example, an interference signal with the measurement light returned from the first depth region and an interference signal with the measurement light returned from the second depth region different from the first depth region. Here, if both the first depth region and the second depth region are within the subject eye, it is possible to collectively obtain OCT data over a wider range for the depth region.

Further, when an irradiation condition of the measurement light relating to the imaging range is changed, a case where an optical path length of the measurement light is greatly changed compared with a size of the subject eye is considered. As an example, there may be a case or the like where an attachment thereinafter, referred to as a "measurement attachment") is inserted into or removed from the measurement optical path in order to change the irradiation condition of the measurement light. In this case, an optical path length difference between the first divergence optical path and the second divergence optical path may be determined according to the amount of change in the optical path length of the measurement optical path accompanying insertion and removal of the measurement attachment. In this case, in a case where intensity of one interference signal is satisfactorily obtained among the interference signal due to the reference light passing through the first divergence optical path and the interference signal due to the reference light passing through the second divergence optical path, intensity of the other interference signal is weak enough. Thus, OCT data in a desirable imaging range is satisfactorily obtained even before and after the irradiation condition relating to the imaging range is switched.

<Switching Between First Divergence Optical Path and Second Divergence Optical Path>

Further, in a case where the third waveguide is diverged to the first divergence optical path and the second divergence optical path, the reference attachment may include a switch (an example of a drive unit) that switches an optical path through which the reference light from the beam splitter is guided, between the first divergence optical path and the second divergence optical path. Thereby, the detector may be able to selectively detect one of an interference signal due to the reference light from the first divergence optical path and an interference signal due to the reference light from the second divergence optical path.

The switch may be switched by, for example, a control unit (processor) of the OCT apparatus, according to a state (insertion state/retraction state) of a light guide optical system. That is, the switch may be driven and controlled such that the reference light from the beam splitter is guided to the first divergence optical path in the retraction state and the reference light from the beam splitter is guided to the second divergence optical path in the insertion state. Such a method of compensating the amount of changes in an optical path length in the measurement optical path is advantageous in reducing noise.

<Adjustment of Optical Path Length in Third Waveguide>

The reference attachment may further include an optical path length adjustment unit that is driven and controlled to adjust an optical path length of the third waveguide. The optical path length adjustment unit increases or decreases the optical path length of the third waveguide within a predetermined adjustment range. An optical path length difference between the measurement light and the reference light is adjusted by driving and controlling the optical path length adjustment unit. As one example of the optical path length adjustment unit, an optical delay line (optical delay line: ODL) is known.

<For Supply of Power and Control Signal of Reference Attachment Including Switch, ODL, and the Like>

In a case where the reference attachment includes devices such as a switch and an ODL as described above, a conductive wire for supplying power from an external power supply to the device may be provided in the reference attachment. Further, a conductive wire for inputting a control signal from the control unit (processor) of the OCT apparatus to the device may be provided in the reference attachment. In addition, a connection terminal for electrically connecting each conductive wire to a terminal of the OCT apparatus body may be provided in the reference attachment.

<Attachment/Detachment Method>

Generally, since the OCT optical system is housed inside an apparatus, it is considered that the apparatus needs to be disassembled so as to attach and detach the reference attachment. Accordingly, a person who performs work (hereinafter, referred to as "attachment/detachment work") of adjusting the OCT optical system by attaching or detaching the reference attachment is hereinafter referred to as a "worker". In the attachment/detachment work, the reference attachment is attached to and detached from the OCT optical system such that the third waveguide of the reference attachment is inserted between or removed from the end portion of the first waveguide and the end portion of the second waveguide in tire OCT optical system.

Here, since an initial state (for example, state at the time of shipment from a factory) of the OCT apparatus described above is considered to be one of the following two types, the attachment/detachment work will be described for each initial state.

<First Initial State>

As a first initial slate, the reference attachment is considered to be previously attached to the OCT optical system. At this time, for example, a worker removes the previously attached reference attachment from the OCT optical system and replaces the reference attachment with a new reference attachment.

The new reference attachment includes a third waveguide different from the previously attached reference attachment. For example, the third waveguide of the new reference attachment may have a different optical path length from the third waveguide of the previously attached reference attachment. In this case, at least one reference attachment may include a plurality of third waveguides. At this time, among the two reference attachments to be replaced, at least one waveguide has a different optical path length from any other. Further, in terms of presence or absence of an element that is driven and controlled by a control unit such as a switch and an ODL, the third waveguide of the new reference attachment may differ from the third waveguide of the previously attached reference attachment.

Further, if the end portion of the first waveguide and the end portion of the second waveguide of the OCT optical system can be directly connected, the attachment/detachment work may be performed as follows. That is, in the attachment/detachment work, the optical path length of the reference optical path may be adjusted by connecting the end portions of the first waveguide and the second waveguide to each other after the previously attached reference attachment is removed by the worker.

<Second Initial State>

As a second initial state, a case where the OCT apparatus does not include the reference attachment is considered. In this case, the first waveguide and the second waveguide are directly connected in a separable manner.

In this case, a worker separates the first waveguide and the second waveguide, and then attaches the reference attachment such that the third waveguide is inserted therebetween. Further, in this case, as illustrated in a fifth example which will be described below, an optical path length of a measurement optical path may be extended. In the fifth example, as an example, a pair of optical connectors is provided on a fiber forming the measurement optical path. When an optical path of the measurement optical path is extended, the optical connectors are separated, and an optical path extension attachment is attached therebetween. Thereby, the optical path length of the measurement optical path is extended. A specific example of the optical path extension attachment includes a patch fiber (also referred to as a patch cord) and the like.

Through the attachment/detachment work, the worker can easily expand or change the imaging range of the OCT apparatus.

In a case where the OCT optical system and the reference attachment each include the first connector and the second connector, it is easy to appropriately connect the waveguides. Therefore, burden of the worker in the attachment/detachment work is reduced.

Example

Hereinafter, the optical coherence tomography (OCT) apparatus illustrated in FIGS. 1 to 5 will be described as a first example. FIG. 1 illustrates the OCT apparatus of the first example.

The OCT apparatus of the first example is suitable for imaging OCT data of fundus.

Figure 3:
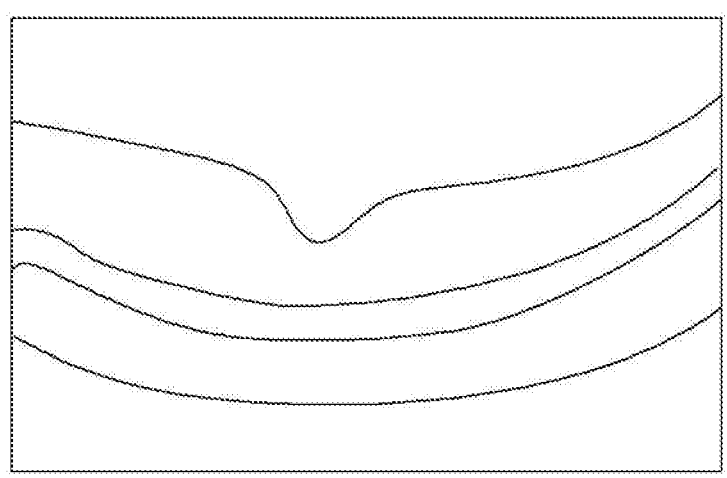
FIG. 3 is an example, of a B-scan image of a fundus obtained by imaging a central region.

In an initial state, in the OCT apparatus, a reference attachment 200 is previously attached to an interference optical system (OCT optical system of the present embodiment) 100. At this time, in the present example, the OCT apparatus can obtain the OCT data of the fundus in a state where an angle-of-view switching attachment 160 is not attached (retraction state) as represented as a symbol A. For example, OCT data in a central portion of the fundus is obtained as illustrated in FIG. 3.

Meanwhile, if the angle-of-view switching attachment 160 is attached as represented as a symbol B in a state where the reference attachment 200 is attached (attached state), the measurement optical path is extended, and thereby, an optical path length difference between the measurement optical path and the reference optical path does not correspond to the fundus. As a result, it is not possible to obtain the OCT data of the fundus satisfactorily.

Figure 4:
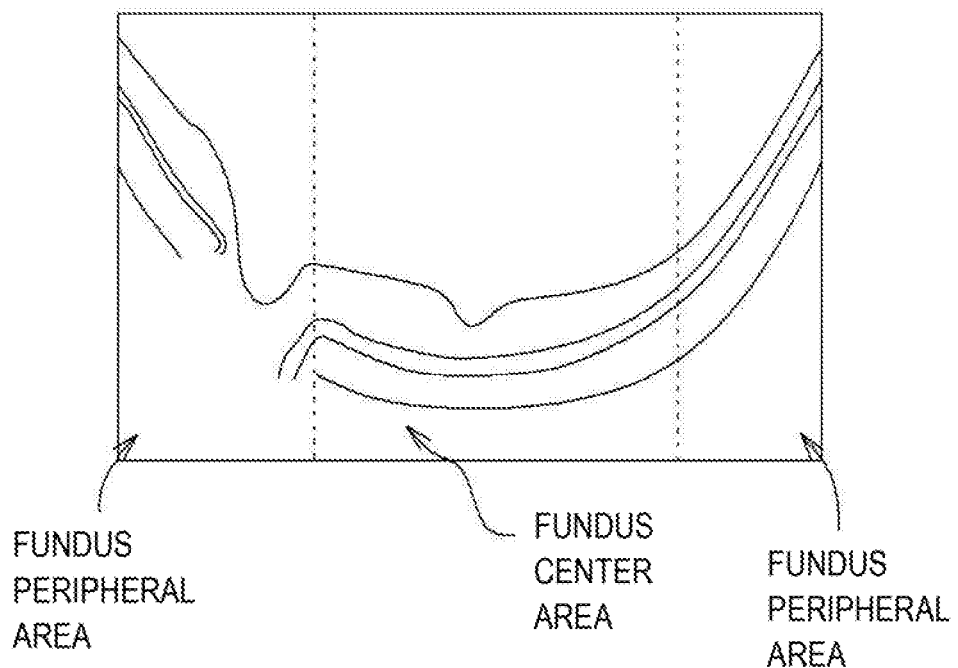
FIG. 4 is an example of a B-scan image of a fundus obtained by imaging a wide-angle region.

Meanwhile, the previously attached reference attachment 200 is replaced with another reference attachment 210 by a worker, and thereby, the OCT data of the fundus can be satisfactorily obtained in a state where the angle-of-view switching attachment 160 is attached. That is, for example, it is possible to obtain OCT data for a region including a fundus center area and a fundus peripheral area as illustrated in FIG. 4. Further, a reference attachment 210 includes a third waveguide corresponding to the retraction state, in addition to the third waveguide corresponding to the attached state. As a result, imaging in the retraction state can also be handled. As such, by replacing the previously attached reference attachment 200 with another reference attachment 210, the OCT apparatus can obtain the OCT data of the fundus in both the attached state and the retraction state.

Hereinafter, a detailed configuration of the OCT apparatus of the first example will be described.

For example, the OCT apparatus according to the first example has spectra domain OCT (SD-OCT) as a basic configuration.

Figure 2:
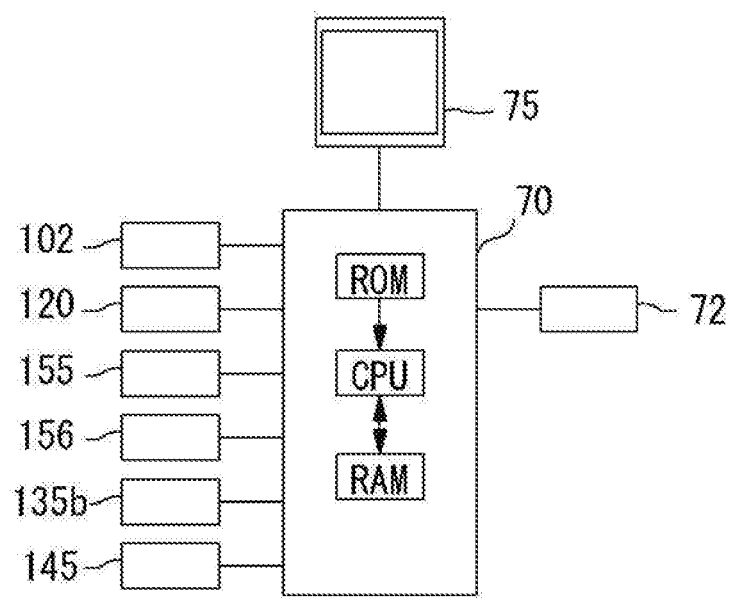
FIG. 2 is a block diagram illustrating a control system of the first example.

An OCT apparatus includes a light source 102, an interference optical system (OCT optical system) 100, and a calculation controller (calculation control unit) 70 (refer to FIG. 2). Additionally, as shown in FIG. 2, a memory 72, a display unit 75, a front image observing system and a fixation target projecting system (not shown) may further be provided in the OCT apparatus. The calculation controller (hereinafter, a control unit) 70 is connected to the light source 102, the interference optical system 100, the memory 72, and the display unit 75.

The interference optical system 100 guides the measurement light to an eye E by a light guide optical system 150. The interference optical system 100 guides the reference light to a reference optical system 110. The interference optical system 100 causes a detector (light receiving element) 120 to receive an interference signal light that is obtained due to interference of the reference light with the measurement light reflected from the eye E. The interference optical system 100 is mounted in a housing (apparatus main body) (not shown), and the housing moves three-dimensionally with respect to the eye F by a known alignment moving mechanism via an operation unit such as a joystick. In this manner, alignment may be performed with respect to the subject eye.

The SD-OCT type may be used for the interference optical system 100. A light source that emits a light-flux having a short coherence length is used as the light source 102, and a spectroscopic detector that performs spectroscopic dispersion and detects a spectral interference signal for each wavelength component is used as the detector 120.

A coupler (splitter) 104 is used as a first beam splitter and splits light emitted from a light source 102 into the measurement optical path and the reference optical path. The coupler (Fiber Coupler) 104 guides, for example, the light from the light source 102 to an optical fiber 152 on the measurement optical path side and also guides the light onto the reference optical path side via the fiber 106.

<Light Guide Optical System>

The light guide optical system 150 is provided to guide the measurement light to the eye E. For example, in the light guide optical system 150, the optical fiber 152, a collimator lens 154, a variable beam expander 155, an optical scanner 156, and an objective lens system 158 (the objective optical system in the example) are provided in this order. In this case, the measurement light is emitted from an emission end of the optical fiber 152 and becomes a parallel beam by the collimator lens 154, Then, the light travels toward the optical scanner 156 in a state of having a desired light-flux diameter by the variable beam expander 155. The eye E is irradiated with the beam passing through the optical scanner 156 via the objective lens system 158. A first turning point P1 is formed at a conjugated position of the optical scanner 156 with respect to the objective lens system 158. The anterior portion is positioned at the turning point P1, and thereby the measurement reaches the fundus without vignetting. In addition, the fundus is scanned with the measurement light depending on the operation of the optical scanner 156. In this case, the measurement light is scattered and reflected by tissue of the fundus.

The optical scanner 156 may scan the eye E with the measurement light in XY directions (transverse directions). For example, the optical scanner 156 is configured of two galvano mirrors, and a reflection angle of the mirror is adjusted optionally by a driving mechanism. A reflection (traveling) direction of the light-flux emitted from the light source 102 changes, and the fundus is scanned in any optional direction. For example, as the optical scanner 156, an acousto-optic modulator (AOM) or the like that changes the traveling (deflection) direction of light may be used, in addition to a reflective mirror (a galvano mirror, a polygon mirror, or a resonant scanner).

Scattered light (reflected light) of the measurement light from the eye E travels back via a path used during light projection, is incident to the optical fiber 152, and reaches the coupler 104. The coupler 104 guides the light from the optical fiber 152 to a light path toward the detector 120.

In the first example, an optical path length due to an optical path reciprocating from the coupler 104 to a fundus of a subject eye E via the fiber 152 and the light guide optical system 150 and an optical path of the fiber 105 becomes a part to be considered as an optical path length of the measurement optical path.

<Angle-of-View Switching Attachment>

Next, the angle-of-view switching attachment 160 will be described. The angle-of-view switching attachment 160 is attached to and detached from a housing surface of the OCT apparatus as an example. A lens barrel including, an attachment optical system 160a may be the angle-of-view switching attachment 160 in the present example. By attaching and detaching the angle-of-view switching attachment 160, the attachment optical system 160a is inserted and removed between an object optical system 158 and a subject eye E.

The attachment optical system 160a may include a plurality of lenses 161 to 164. Here, a lens having principal power in the attachment optical system 160a shown in FIG. 1 is the lens 164 placed in front of the subject eye. An insertion/removal position of at least the lens 164 is between the first turning point P1 that is formed by the objective optical system 158 and the subject eye E. At least the lens 164 turns the measurement light passed through the first turning point P1 toward an optical axis L, and thereby a second turning point P2 is formed at a conjugated position of the optical scanner 156 with regard to the attachment optical system 160a and the objective optical system 158. In other words, the attachment optical system 160a is an optical system that relays the turning point P1 to the turning point P2.

In the example, a solid angle of the measurement light at the second turning, point P2 is larger than a solid angle at the first turning point P1. For example, the solid angle at the second turning point P2 is increased as twice or more as the solid angle at the first turning point P1. In the example, it is possible to perform scanning at an angle of view of about 60° in the retraction state, and it is possible to perform scanning at an angle of view of about 100° in the insertion state.

The variable beam expander 155 is the light-flux diameter adjusting unit in the example. As an example, the variable beam expander 155 may include a plurality of lenses that form a both-side telecentric optical system and may be configured to switch a light-flux diameter by changing a lens space by an actuator. The variable beam expander 155 adjusts the light-flux diameter of the measurement light based on an instruction from the control unit 70.

If the light-flux diameter of the measurement light that is guided from the variable beam expander 155 to the optical scanner 156 is constant between the insertion state and the retraction state, the spot size of the measurement light is proportional to the angle of view on the fundus. Therefore, the resolving power is more degraded in the insertion state than in the retraction state. In the example, the control unit 70 drives the variable beam expander 155 according to the insertion and the removal of the attachment optical system and more decreases the light-flux diameter in the insertion state than in the retraction state. A rate of the light-flux diameters (light-flux diameters in the variable beam expander 155) in the insertion state and the retraction state is inversely proportional to the angle of view in the insertion state and the retraction state, and thereby at is, possible to suppress a change in resolving power based on the insertion and removal of the attachment optical system 160a.

Incidentally in order to secure a sufficient operation distance, the attachment optical system 160a needs to cause the measurement light, to be tuned from a position having a sufficient light beam height toward the optical axis L. In addition, in order to suppress an aberration caused by the attachment optical system 160a within a permissible range, power of the lenses included in the attachment optical system 160a is limited. Hence, it is difficult to shorten the optical path length of the attachment optical system 160a.

Although there is an OCT apparatus in the related art that is configured to adjust the optical path length difference between the reference light and the measurement light, there is no OCT apparatus that has an adjustment range that is applicable to the insertion and removal of the attachment optical system 160a. For example, in the related art, there has been known a technology in which an optical adapter is installed such that it is possible to perform imaging an anterior portion in fundus imaging OCT (for example, see "JP-A-2011-147612" or the like by the present applicant). However, the optical adapter does not relay the turning point formed by an optical system of an apparatus main body, and there is no demand for a wide-angle scanning range. Therefore, the optical adapter can be formed to have a relatively short optical path length. Further, a position of an image surface is changed from the fundus to the anterior portion in response to insertion of the optical adapter. Hence, there is no need to significantly adjust the optical path length difference in response to the insertion of the optical adapter.

<Reference Optical System>

The reference optical system 110 generates the reference light that is combined with fundus reflection light of the measurement light. The reference light passing through the reference optical system 110 is coupled and interferes with light from the measurement light path by a coupler (Fiber coupler) 148. The reference optical system 110 may be one of a Michelson type or a Mach-Zehnder type.

The reference optical system 110 shown in FIG. 1 is formed by a transmission optical system. In this case, the reference optical system 110 does not cause the light from the coupler 104 to return but transmits the light, thereby guiding the light to the detector 120. The reference optical system 110 is not limited thereto and may be formed by a reflection optical system and guide the light from the coupler 104 to the detector 20 by causing the light to be reflected from the reflection optical system, for example.

An optical path length of a continuous optical path from the coupler 104 to the coupler 148 is a part to be considered as an optical path length of the reference optical path in the present example. The reference optical path is largely divided into a first waveguide, a second waveguide, and a third waveguide. Among those, the first waveguide and the second waveguide are provided in the interference optical system 100. As illustrated in FIG. 1, among the reference optical paths included in the interference optical system 100, the optical path formed on the coupler 104 side is referred to as the first waveguide, and the optical path formed on the photodetector 120 is referred to as the second waveguide. Meanwhile, the third waveguide is provided in the reference attachment 200 and the reference attachment 210.

The first waveguide in FIG. 1 includes the coupler 104, the fiber 106, and a connector 108, The connector 108 is provided in an end portion of the first waveguide opposite to the coupler 104. As will be described below, the connector 108 is attachable to and detachable from a connector 201 of the reference attachment 200 and a connector 211 of the reference attachment 210.

The second waveguide in FIG. 1 includes a connector 131, a fiber 133, an ODL 135, a fiber 137, an attenuator 141, a fiber 143, a polarization adjuster 145, a fiber 147, and a coupler 148. As will be described below, the connector 131 is attachable to and detachable from the connector 205 of the reference attachment 200 and the connector 217 of the reference attachment 210.

The ODL 135 is driven and controlled to adjust the optical path length difference between the measurement light and the reference light. As an example, the ODL 135 includes a mirror 135a having two orthogonal surfaces, and an actuator 135b. The optical path length of the reference optical path can be increased or decreased by being moved in an arrow direction by the actuator 135b.

Of course, the configuration in which the optical path length difference between the measurement light and the reference light is adjusted is not limited to this. For example, in the light guide optical system 150, the optical path length of the measurement light is adjusted by moving the collimator lens 154 and the emission end of the fiber 152 integrally, and as a result, the optical path length of the measurement light and the reference light may be adjusted.

The attenuator 141 attenuates the amount of reference light. The attenuator 141 adjusts a light amount balance between the measurement light and the reference light.

The polarization adjuster 145 adjusts polarization of the reference light. The polarization adjuster 145 corrects a polarization shift between the measurement light and the reference light.

Next, third waveguides 200 and 210 illustrated in FIG. 1 will be described. As described above, the third waveguide is provided in the reference attachment 200 and the reference attachment 210.

<Reference Attachment 200 Attached in Initial State>

The reference attachment 200 includes the connector 201, a fiber 203, and the connector 205. The connector 201 and the connector 205 are attached to both end portions of the one fiber 203. Thereby, a single third waveguide is formed.

In the reference attachment 200, the third waveguide is connected to the first waveguide in the interference optical system 100 by attaching the connector 201 to the connector 108 of the interference optical system 100. Further, the third waveguide is connected to the second waveguide in the interference optical system 100 by attaching the connector 205 to the connector 131 of the interference optical system 100.

The optical path length of the fiber 203 and the optical path length of the measurement optical path in the retraction state of the angle-of-view switching attachment 160 substantially match each other in a difference between the optical path lengths of the first waveguide and the second waveguide. As a result, in the retraction state of the angle-of-view switching attachment 160, a satisfactory interference signal regarding a depth region including the fundus can be obtained.

<Reference Attachment 210 to be Attached to OCT Apparatus by Replacement Work>

The reference attachment 210 includes the third waveguides diverged to two. One of the diverged waveguides is referred to as a first divergence optical path, and the other is referred to as a second divergence optical path. Since the first divergence optical path and the second divergence optical path have different optical path lengths, an optical path length of the third waveguide passing through the first divergence optical path is different from an optical path length of the third waveguide passing through the second divergence optical path.

The reference attachment 210 includes, as an example, the connector 211, a fiber 212, a coupler 213, a fiber 214, a coupler 215, a fiber 216, a connector 217, and a fiber 218.

Reference light passing through the connector 211 and the fiber 212 is guided to each of the fiber 214 and the fiber 218 by the coupler 213. Hereinafter, for the sake of convenience, an optical path due to the fiber 218 is referred to as the first divergence optical path, and an optical path due to the fiber 214 is referred to as the second divergence optical path. The fiber 214 and the fiber 218 are connected to the coupler 215. Thereby, the two divergence optical paths are coupled to the optical path passing through the fiber 216 and guided to the connector 217.

As such, in the reference attachment 210, the coupler 213 simultaneously guides the reference light to the fiber 214 and the fiber 218. (that is, the two divergence Optical paths). Further, the reference light passing through the two divergence optical paths IS simultaneously guided to the coupler 148 of the OCT optical system 100 via the connector 217 and the connector 131 and is combined with the measurement light (fundus reflection light) by the coupler 148.

Here, in the reference attachment 210, it is assumed that the third waveguide passing through the first divergence optical path (that is, passing through the fiber 218) matches the optical path length of the third waveguide in the reference attachment 200. That is, the first divergence optical path is used for imaging in a retraction state of the angle-of-view switching attachment 160.

Meanwhile, the second divergence optical path is used for imaging in an insertion state of the angle-of-view switching attachment 160 inserted. The optical path length (that is, the optical path length of the fiber 214) of the second divergence optical path is longer than the optical path length (That is, the optical path length of the fiber 218) of the first divergence optical path by the optical path length (more specifically, the reciprocating optical path length. The same applies hereinafter) of the angle-of-view switching attachment 160.

An attenuator (not illustrated) may be provided on one or both of the first divergence optical path and the second divergence optical path in order to correct the amount of light of each of the first divergence optical path and the second divergence optical path. In the present example, since the amount of measurement light is changed by the attachment 16) in the insertion state of the angle-of-view switching attachment 160, it is preferable to provide an attenuator on the second divergence optical path corresponding to the insertion state.

Further, in the first example, a reference optical path adjustment unit 135 is provided on the second waveguide of the interference optical system 100, that is, on a common optical path of the first divergence optical path and the second divergence optical path. Accordingly, an optical path length difference between the measurement optical path and the reference optical path, which is an optical path length difference relating to an individual difference between eye axial lengths, can be adjusted collectively for both the first divergence optical path and the second divergence optical path.

It is preferable that an adjustment range of the optical path length in the reference optical path adjustment unit 135 is set to be sufficiently shorter than the optical path length difference between the fiber 214 and the fiber 218 (in other words, the optical path length difference between the first divergence light path and the second divergence light path).

<Light Detector>

The detector 120 is provided to detect interference of the light from the measurement light path with the light from the reference light path. In the first example, the detector 120 is a spectroscopic detector and includes an optical spectrometer and a line sensor, for example, in which the measurement light and the reference light which are coupled by the coupler 148 are scattered by the optical spectrometer and are received in a different region (pixel) of the line sensor for each wavelength. Consequently, an output for each pixel is obtained as a spectral interference signal.

Since a curvature of the fundus does not necessarily match an image forming surface of the measurement light, and a displacement between both of a fundus center area and a fundus peripheral area increases in at least one of the areas in the insertion state of the attachment optical system 150, it is preferable to secure a sufficient depth range in the light detector in consideration of the displacement. For example, in the SD-OCT, it is preferable to provide a line camera having a sufficient number of pixels with respect to an anticipated depth range. In addition, the following configuration may be further employed as "modification examples".

<Obtainment of Depth Information>

The control unit 70 performs processing (Fourier analysis) on a spectral signal detected by the detector 120 and obtains OCT data of the subject eye.

The spectral signal (spectral data) may be rewritten as a function of a wavelength $\lambda$ and may be converted to an equal interval function I (k) with regard to a wave number k ($=2\pi/\lambda$. Alternatively, the spectral signal may be acquired as an equal interval function I (k) with regard to the wave number k from the beginning (a k-clock technology), The calculation controller may perform Fourier transform of the spectral signal in, a space having the wave number k, thereby obtaining OCT data in a depth (Z) region.

Further, information after the Fourier transform may be obtained as a signal containing a real component and an imaginary component in a Z space. The control unit 70 may obtain absolute values of the real component and the imaginary component in the signal in the Z space, thereby obtaining the OCT data.

Here, an interference signal will be described in a case where the reference attachment 210 in which the third waveguide is diverged to two is attached to the interference optical system 100.

In this case, reference light passing through the first divergence optical path and reference light passing through the second divergence optical path are simultaneously guided to the coupler 148, and each reference light is combined with the measurement light, There is a large optical path length difference between the first divergence optical path and the second divergence optical path, which is approximately the same as the optical path length (the optical path length of the attachment optical system 160*a*) of the angle-of-view switching attachment 160. Accordingly, although one of the reference light passing through the first divergence optical path and the reference light passing through the second divergence optical path is likely to cause interference with the measurement light, the other is unlikely to cause the interference. Although a spectral interference signal from the detector 120 includes a component due to the reference light passing through the first divergence optical path and a component due to the reference light passing through the second divergence optical path, one component according to a state of the light guide optical system 150 among two types of components is obtained as a signal that is significantly stronger than the other component. As a result, it is possible to obtain satisfactory OCT data regardless of the state of the light guide optical system 150. That is, by including a plurality of reference optical paths having an optical path length difference corresponding to the angle-of-view switching attachment 160, the OCT apparatus according to the example compensates for the amount of change of the optical path length difference in the measurement optical path, which is the amount of change according to attachment/detachment of the angle-of-view switching attachment 160 regardless of attachment/detachment states of the angle-of-view switching attachment 160.

The reference optical path adjustment unit 135 needs to be controlled to adjust the optical path length difference related to the ocular axial length of the subject eye E, which is the optical path length difference between the measurement light path and the reference tight path, in advance. For example, in the first example, the mirror 135*a* may be moved in a predetermined adjustment range, an interference signal may be obtained at each position, and the position of the mirror 135*a* may be determined on the basis of a position, at which the strength of the interference signal has the highest strength. In a case where the adjustment range of the optical path length in the reference optical path adjustment unit 135 is sufficiently small with respect to the optical path length difference between the first divergence light path and the second divergence light path, at a position in the adjustment range of the reference optical path adjustment unit 135, at which the interference signal has a strength peak, can be uniquely identified.

An insertion removal detection unit that automatically detects attachment/detachment of the angle-of-view switching attachment 160 may be provided, and a control unit may control each unit in the OCT optical system 100 and may perform processing, based on a detection signal from the detection unit. For example, a switching control of a light beam diameter by a variable beam expander 155, a setting control of a zero delay position by a reference optical path adjustment unit 135, change processing of a dispersion amount of the optical system between the measurement optical path and the reference light, and the like which are described above may be performed as appropriate. An insertion detection unit may be a sensor disposed near the object optical system 158.

It is needless to say that an examiner may input information that identifies the state of the light guide optical system (the insertion state/retraction state of the attachment optical system) on a user interface (UI) of the OCT apparatus, and thereby the control unit may perform the control and the processing of each member in the OCT optical system 100 based on the corresponding information.

<Case>

Figure 5:
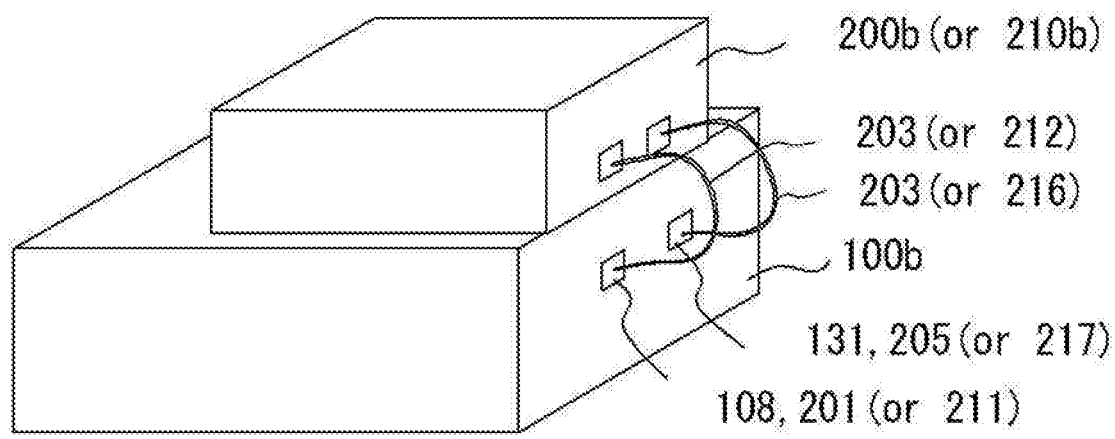
FIG. 5 is a diagram illustrating a case provided in an interference optical system and a reference attachment.

As illustrated in FIG. 5, the reference attachments 200 and 210 may include cases 200*b* and 210*b* respectively. The cases 200*b* and 210*b* house at least various fibers and couplers. Further, in the present example, the OCT apparatus may include a case 100*b* that houses each portion of the interference optical system 100 from the coupler 104 to the coupler 148. However, in order to attach and detach connectors between the OCT optical system 100 and the reference attachments 200 and 210, for example, a part or all of the connectors 108 and 131, the connectors 201 and 205, and the connectors 211 and 217 may be exposed outside the case. Since the fibers in the interference optical system 100 and the reference attachments 200 and 210 are housed in the cases 100*b*, 200*b*, and 210*b*, each portion is well protected during attachment/detachment work and transport of the reference attachments 200 and 210.

<Calibration>

Since the optical path length difference between the first divergence optical path and the second divergence optical path is a known value, the optical path length difference may be used for calibration in a depth direction, for example. As an example, a predetermined sample such as a model eye is imaged, and an interval in the depth direction between the OCT data due to the reference light passing through the first branch optical path and the OCT data due to the reference light passing through the second branch optical path is obtained. A scale of the OCT data in the depth direction may be adjusted such that the interval has a predetermined value according to the optical path length difference.

Second Example

Figure 6:
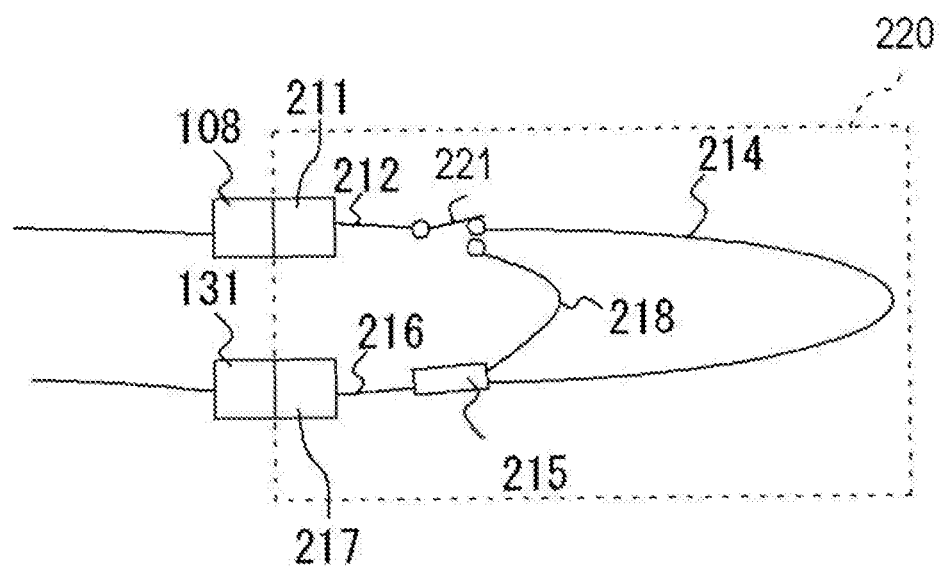
FIG. 6 is a diagram illustrating a reference attachment according to a second example.

Next, a second example will be described with reference to FIG. 6. FIG. 6 illustrates a reference attachment 220 according to the second example. The same members as those of the first example are denoted by the same reference numerals, and details thereof are omitted.

The reference attachment 220 according to the second example is partially different from the reference attachment 210 according to the first example. As described above, the reference attachment 210 according to the first example simultaneously guides the reference light passing, through the first divergence optical path and the reference light passing through the second divergence optical path to the detector 120. In contrast to this, the reference attachment 220 according to the second example selectively guides the reference light passing through the first divergence optical path and the reference light passing through the second divergence optical path to the detector 120.

In detail, in the second example, an optical switch 221 is provided instead of the coupler 213 in the first example. The optical switch 221 may be, for example, a mechanical switch or a MEMS switch. The optical switch 221 is used for selectively guiding the reference light passing through the connector 211 and the fiber 212 to one of the optical fiber 218 forming the first divergence optical path and the optical fiber 214 forming the second divergence optical path. In the second example, since the reference light is selectively guided to one of the first divergence optical path and the second divergence optical path, the more sufficient amount of the reference light can be ensured as compared with the first example. Further, noise in the interference signal is reduced.

Third Example

Figure 7:
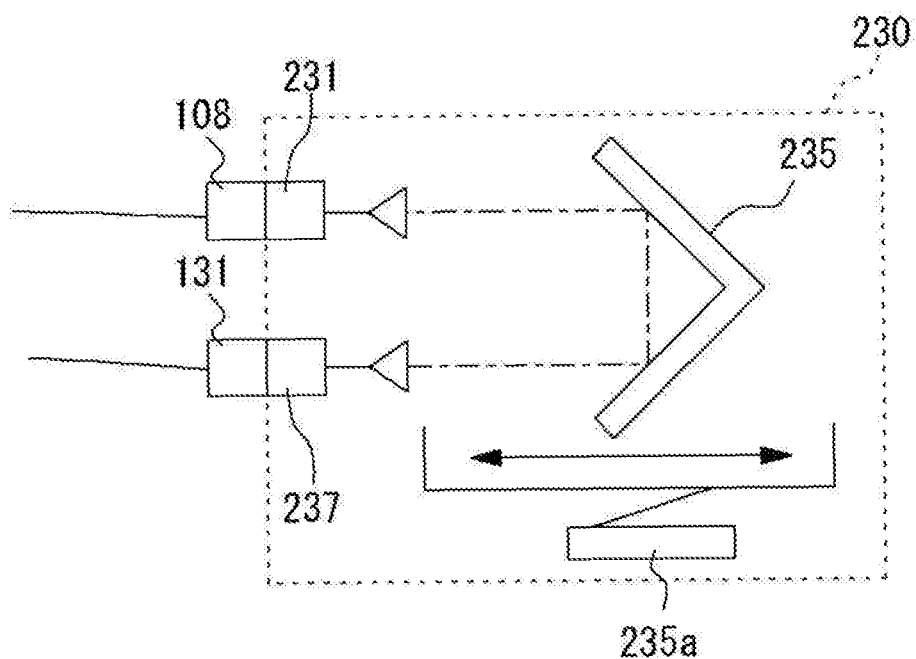
FIG. 7 is a diagram illustrating a reference attachment according to a third example.

Next, a third example will be described with reference to FIG. 7. FIG. 7 illustrates a reference attachment 230 according to the third example. In the reference attachment disclosed in the first and second examples, the optical path length of the third waveguide is predetermined, but the reference attachment 230 of the third example can adjust the optical path length of the third waveguide to any length. A degree of freedom of the imaging range in the OCT apparatus is further improved.

The third attachment 230 includes a connector 231, an ODL unit 235, and a connector 237. The ODL unit 235 includes a mirror 235 having two orthogonal surfaces, and an actuator 235a. The optical path length of the third waveguide increases or decreases by moving the mirror 235 in an arrow direction by using the actuator 235a. The third attachment 230 may further include a fiber or the like.

Fourth Example

Next, a thumb example will be described with reference to FIGS. 8A and 8B. In the above-described examples, an optical connector is provided at each end portion of the first to third waveguides. In the fourth example, each waveguide is connected without using an optical connector.

Figure 8A:
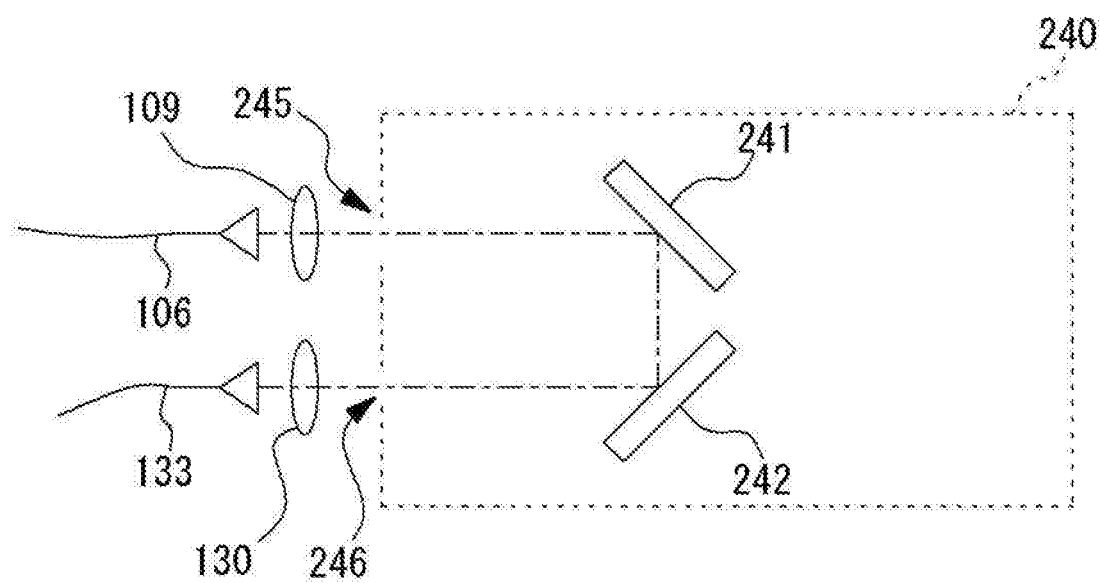
FIG. 8A illustrates one of reference attachments according to a fourth example, and end portions of a first waveguide and a second waveguide.
Figure 8B:
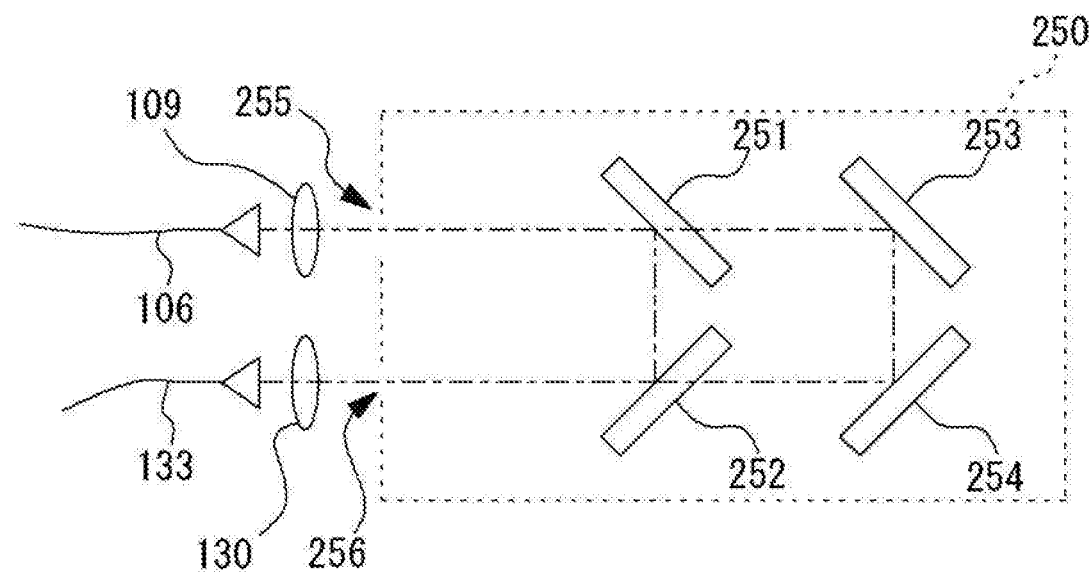
FIG. 8B illustrates a reference attachment different from the reference attachment of FIG. 8A among the reference attachments according to the fourth example and illustrates end portions of a first waveguide and a second waveguide.

FIGS. 8A and 8B illustrate reference attachments 240 and 250 according to the fourth example, and end portions of the first waveguide and the second waveguide in the interference optical system 100. Here, the reference attachment 240 illustrated in FIG. 8A corresponds to the reference attachment 200 in the first example. The reference attachment 250 illustrated in FIG. 8B corresponds to the reference attachment 210 in the first example. That is, the reference attachment 250 includes the third waveguide diverged to two.

As illustrated in FIGS. 8A and 88, the end portion (for example, a cut portion) of the fiber 106 forming the first waveguide and the end portion of the fiber 133 forming the second waveguide are exposed to the air regardless of attachment/detachment of the reference attachments 240 and 250. Each end portion may be positioned within the case 100b. The interference optical system 100 further includes collimating lenses 109 and 130. The reference light from the fiber 106 is emitted to the reference attachments 240 and 250 via the collimating lens 109. In a case where the reference attachments 240 and 250 include cases, the cases may be provided with openings 245, 246, 255, and 256 for making the reference light pass (see FIGS. 8A and 8B).

The reference fight from the third waveguides of the reference attachments 240 and 250 is incident on the end portion of the fiber 133 via the lens 130.

As illustrated in FIG. 8A, the reference attachment 240 includes, at least mirrors 241 and 242. The two mirrors 241 and 242 form an optical path that turns back the reference light in the case of the reference attachment 240. This optical path becomes the third waveguide in the reference attachment 230.

As illustrated in FIG. 8B, the reference attachment 250 includes at least half mirrors 251 and 252 and mirrors 253 and 254. Thereby, two optical paths of an optical path that is turned back by the two half mirrors 251 and 252, and an optical path that is turned back by the two mirrors 253 and 254 are formed. The third waveguide is diverged to the first waveguide and the second waveguide by the two half mirrors 251 and 252. The optical path on a reflection side of the half mirror 251 is the first divergence optical path, and the optical path on a transmission side is the second divergence optical path. Each of the half mirrors 251 and 252 adjusts a light amount ratio between the reference light passing through the first divergence optical path and the reference light passing through the second divergence optical path. That is, a branch ratio of the half mirrors 251 and 252 may be determined such that a desirable light amount ratio is realized. In this case, an attenuator not required in adjusting the light amount ratio between the reference light passing through the first divergence optical path and the reference light passing through the second divergence optical path. In other words, a change in the light amount ratio between the measurement light and the reference light between the insertion state and the retraction state of the angle-of-view switching attachment 160 is corrected according to the divergence ratio of the half mirrors 251 and 252.

Fifth Example

Figure 9A:
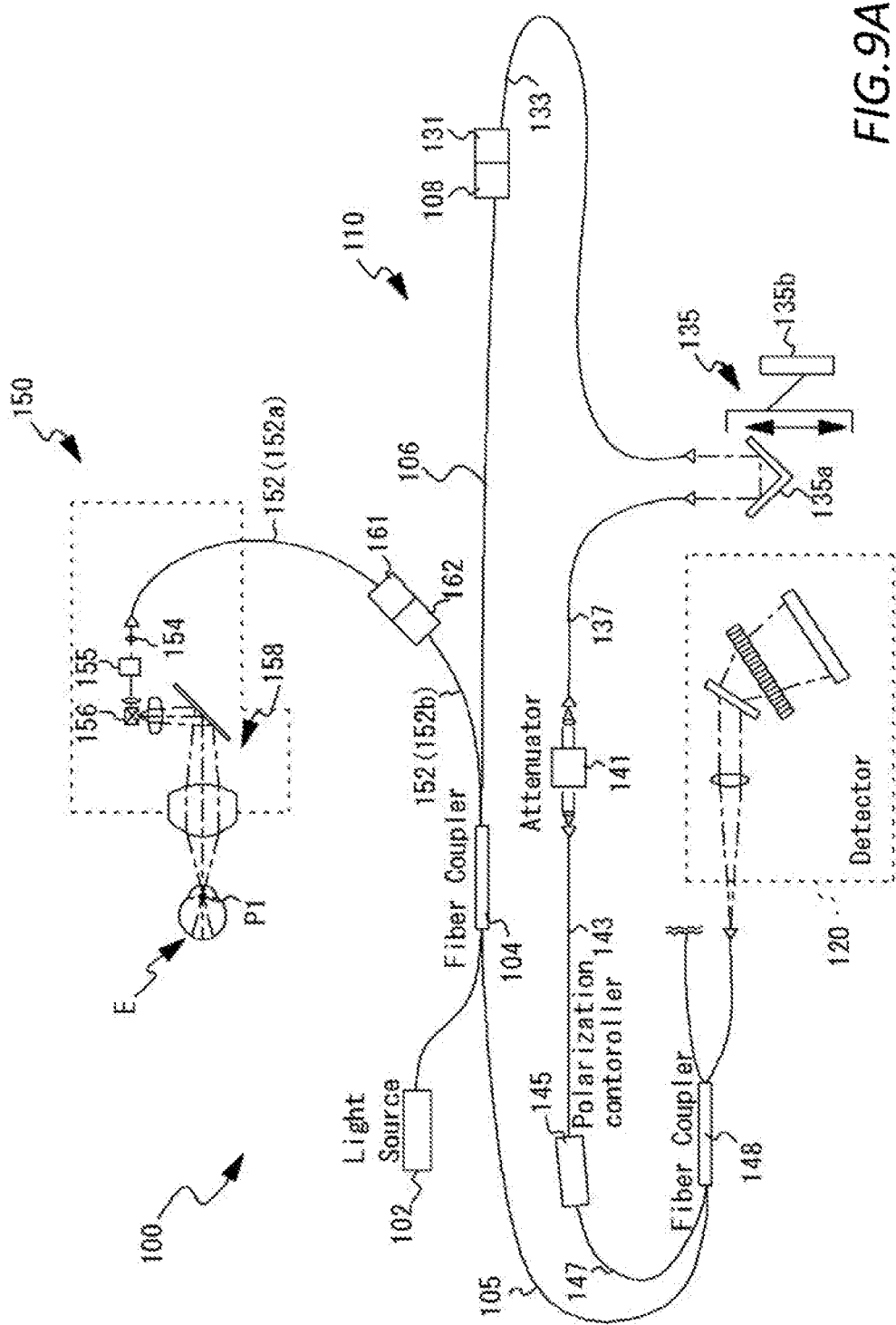
FIG. 9A is a diagram illustrating an initial state of an OCT apparatus according to a fifth example.
Figure 9B:
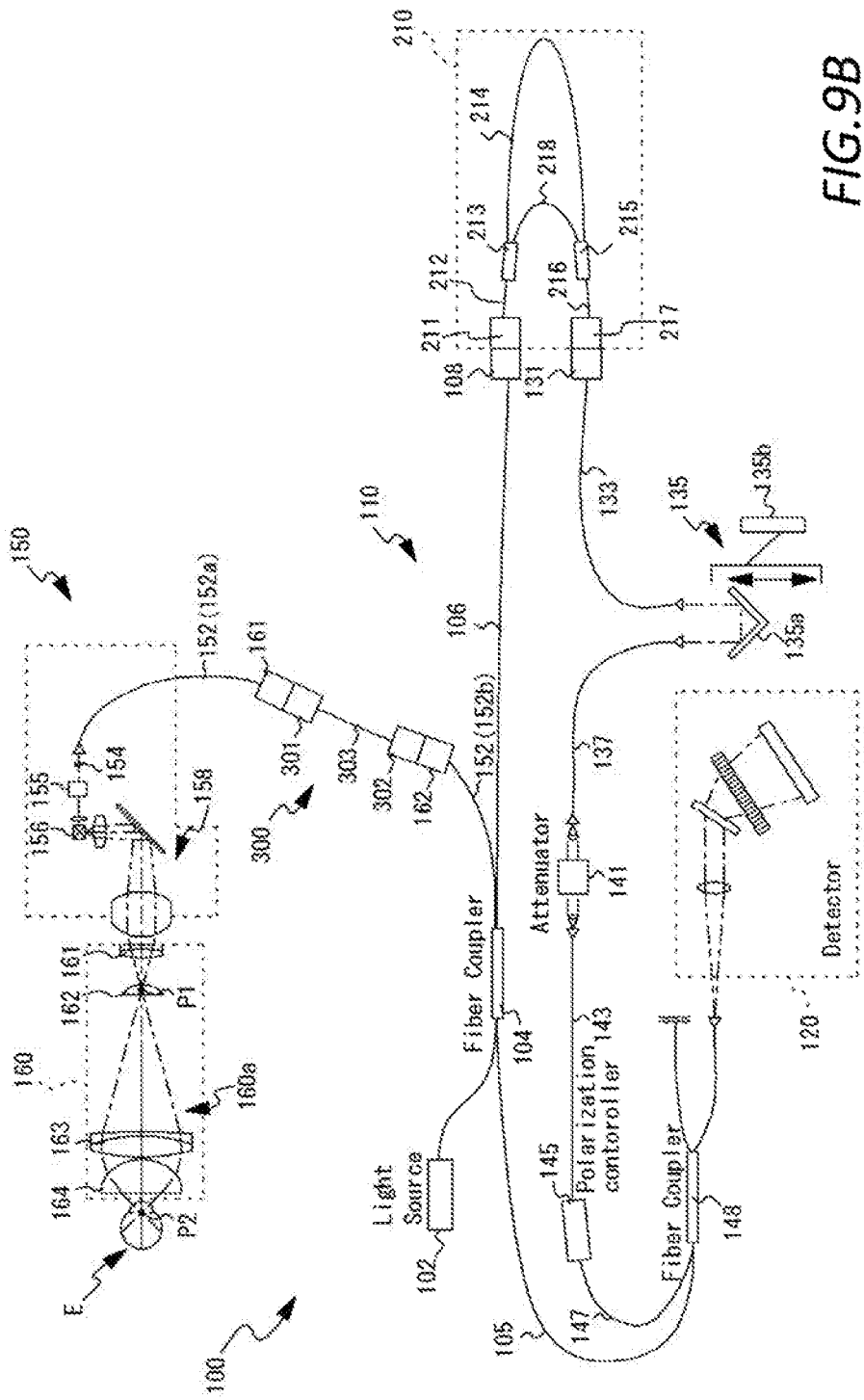
FIG. 9B is a diagram illustrating a state in which a reference attachment and an angle-of-view switching attachment are attached to the OCT apparatus according to the fifth example.

Next, a fifth example will be described with reference to FIGS. 9A and 9B. FIG. 9A illustrates an initial state of the OCT apparatus in the fifth example, and FIG. 9B illustrates a state where the reference attachment 210 is attached to the OCT apparatus in the fifth example. In the fifth example, each portion of the reference attachment 210 is the same as in the first example. Meanwhile, the fifth example differs from the first example in the following two points relating to the interference optical system 100.

As a first different point, as illustrated in FIG. 9A, in the fifth example, the first waveguide and the second waveguide forming the reference optical path are directly connected in an initial state of the OCT apparatus. That is, the connector 108 is connected to the connector 131 in the initial state. In the fifth example, further, when the angle-of-view switching attachment 160 is not attached in this state, OCT data of a fundus is imaged. In other words, in the fifth example, at least a part of the optical path length in the interference optical system 100 is different from the optical path in the first example.

The reference attachment 210 which is the same as the reference attachment in the first example is attached to the OCT apparatus in such an initial state. That is, the reference attachment 210 includes the third waveguide having the first divergence optical path and the second divergence optical path. An optical path length difference corresponding to the optical path length of the angle-of-view switching attachment 160 exists between the first divergence optical path and the second divergence optical path. However, in the fifth example, the amount of change in the optical path length between the connector 108 and the connector 131 before and after attaching the reference attachment 210 is larger than the amount of change in the first example. In detail, the amount of change increases by the optical path length of the third waveguide passing through the first divergence optical path. In the same manner as in the first example, in order to obtain satisfactory OCT data of the fundus regardless of attachment/detachment of the angle-of-view switching attachment 160, it is necessary to compensate for the amount of change.

Accordingly, as a second different point, the OCT apparatus according to the fifth example includes connectors 161 and 162. In the fifth example, the fiber 152 connected to the coupler 104 can be separated into a fiber 152a and a fiber 152b via the connectors 161 and 162.

Thereby, an optical path extension attachment 300 can be attached between the connector 161 and the connector 162 as illustrated in FIG. 9B. The optical path extension attachment 300 may be, for example, a patch fiber. In FIG. 9B, the optical path extension attachment 300 includes a fiber 303, and connectors 301 and 302 provided at both ends of the fiber 303. The connectors 301 and 302 are detachable from the connectors 161 and 162, respectively. An optical path length of the optical path extension attachment 300 substantially matches the optical path length of the third waveguide passing through the first divergence optical path in the reference attachment 210. Therefore, in the fifth example, by attaching the optical path extension attachment 300 together with the reference attachment 210 in an initial state, the fundus can be imaged satisfactorily even in any case of when the angle-of-view switching attachment 160 is attached and when the angle-of-view switching attachment 160 is removed, as in the first example.

Other Modification Examples

The present disclosure is described based on the examples described above. However, the present disclosure is not necessarily limited to the above examples and includes various modification examples.

<Plurality of Reference Optical Paths are Formed According to Insertion State>

For example, in the first, second, fourth, and fifth examples, only one reference optical path corresponding to the insertion state of the angle-of-view switching attachment 160 is provided. However, the present disclosure is not limited to this, and a plurality of reference optical paths corresponding to the insertion state may be formed. In more detail, a first reference optical path having, an optical path length set to obtain OCT data including a fundus center area, and a second reference optical path different from the first reference optical path having an optical path length set to obtain OCT data including a fundus peripheral area may be formed as a reference optical path corresponding to the insertion state. In a case where a reference optical path corresponding to each state is provided for each state (here, for each of two states of the insertion state and the retraction state of the angle-of-view switching optical system) of the light guide optical system, the OCT optical system will be provided with three or more reference optical paths.

The optical path length difference between the first reference optical path and the second reference optical path may be set to correspond to an optical path length difference between the measurement lights between the fundus center area and the fundus peripheral area. For example, in consideration of the curvature of the ocular bulb, an optical path length of the second reference optical path may be set to be shorter than an optical path length of the first reference optical path.

In this case, the image processor may obtain OCT data including the fundus center area based on an interference signal of the measurement light guided to the fundus center area and the reference light from the first reference optical path or may obtain OCT data including the fundus peripheral area based on an interference signal of the measurement light guided to the fundus peripheral area and the reference light from the second reference optical path, for example. In this case, the OCT data including the fundus center area and the OCT data including the fundus peripheral area may be continuous to at least one in the transverse direction and a depth direction, for example.

In this manner, the reference optical path corresponding to the fundus center area and the reference optical path corresponding to the fundus peripheral area are set, and thereby it is possible to obtain the OCT data in the wide-angle region at a good signal strength, for example.

The image processor may combine the OCT data including the fundus center area and the OCT data including the fundus peripheral area and may obtain wide-angle OCT data of the fundus of the subject eye (see FIG. 4). Consequently, it is possible to obtain one item of the wide-angle OCT data.

In this case, the optical scanning unit may scan the fundus with the measurement light in one scanning direction, thereby scanning the wide-angle region including the fundus center area and the fundus peripheral area. In this case, a scanned region in the fundus center area and a scanned region in the fundus peripheral area may be continuous to each other in the transverse direction, for example. In addition, the optical scanning unit may be configured to scan the wide-angle region on the fundus with the measurement light to a scannable scan angle, for example. In addition, the optical scanning unit may be disposed substantially at a conjugated position with the pupil of the subject eye and may measure the measurement light with the pupil center as the turning point, for example.

In a case where the optical scanning unit is provided, a wide-angle region including the fundus center area and the fundus peripheral area may be scanned with the measurement light by B scan once by the optical scanning unit, and the OCT data including the fundus center area and the OCT data including the fundus peripheral area may be obtained. Consequently, it is possible to smoothly obtain the OCT data in the wide-angle region, for example.

For example, the OCT optical system may include a first detector corresponding to the fundus center area and a second detector corresponding to the fundus peripheral area. In this case, the first detector is used for detecting an interference signal of the measurement light guided to the fundus center area with the reference light from the first reference optical path. In addition, the second detector is a detector different from the first detector and is used for detecting an interference signal of the measurement light guided to the fundus peripheral area with the reference light from the second reference optical path. In such a configuration, for example, it is possible to use the first detector and the second detector in parallel. As the result, it is possible to reliably detect both items of OCT data of the fundus center area and the fundus peripheral area, and it is possible to smoothly obtain both items of OCT data at a good signal strength.

In the example described above, a case where two reference optical paths are each provided to correspond to the fundus center area and the fundus peripheral area is described; however, the number of reference optical paths is not limited thereto, and three or more reference optical paths may be provided. As an example, a case where the entire fundus is divided into three areas of the fundus center area, the first fundus peripheral area, and the second fundus peripheral area is described. The first fundus peripheral area is disposed on the outer side from the fundus center area, and the second fundus peripheral area is disposed on the outer side more from the first fundus peripheral area.

In this case, the first reference optical path corresponding to the fundus center area, a second reference optical path corresponding to the first fundus peripheral area, and a third reference optical path corresponding to the second fundus peripheral area may be provided in the OCT optical system, for example.

In addition, optical path lengths of the two reference optical paths may be controlled such that the optical system may be caused to switch between a first wide-angle imaging mode and a second wide-angle imaging mode. For example, in the first wide-angle imaging mode, an optical path length in the first reference optical path is set to correspond to the fundus center area, and an optical path length in the second reference optical path is set to correspond to the first fundus peripheral area. On the other hand, in the second wide-angle imaging mode, the optical path length in the first reference optical path is set to correspond to the fundus center area or the first fundus peripheral area, and the optical path length in the second reference optical path is set to correspond to the second fundus peripheral area.

<Angle-of-View Switching Optical System by Reflection System (Mirror System)>

In the example described above, a case where the angle-of-view switching optical system includes at least one lens is described; however, the system is not necessarily limited thereto. The angle-of-view switching optical system may be a mirror system (mirror group). More specifically, the angle-of-view switching optical system may be a decentered mirror system (mirror group) having one or more mirrors. Even in this case, since the optical path length in the measurement optical path changes according to the insertion and retraction of the angle-of-view switching optical system, the optical path length is effectively compensated by the compensation unit.

In the above description, the example of the SD-OCT is described; however, the example is not limited thereto, and the example may be applied to SS-OCT.

In the above description, the OCT apparatus for imaging the subject eye is exemplified; however, the OCT apparatus is not limited thereto, and the embodiment may be applied to an OCT apparatus for imaging OCT data of the subject. The subject is not limited to an eye (an anterior portion, a fundus, or the like). The subject may be a living organism such as skin or a material other than the living organism.

What is claimed is:

1. An OCT system comprising:
an OCT optical system including a beam splitter for splitting light from an OCT light source into a measurement optical path and a reference optical path, a photodetector for detecting a spectral interference signal between measurement light guided onto tissue of a subject eye via the measurement optical path and reference light from the reference optical path, a first waveguide forming a part of the reference optical path, and a second waveguide forming a part of the reference optical path; and
a reference attachment,
wherein the OCT optical system includes first connectors, provided at an end portion of the first waveguide and at an end portion of the second waveguide respectively, for indirectly or directly connecting the first waveguide and the second waveguide,
wherein the reference attachment includes a third waveguide, and second connectors formed at both ends of the third waveguide and configured to be attachable to and detachable from the first connector, and
wherein the reference attachment is attached to and detached from the OCT optical system by attaching and detaching each of the second connectors to and from the first connector to change an optical path length of the reference optical path.

2. The OCT system according to claim 1,
wherein, in the reference optical path, the first waveguide is formed on a side of the beam splitter, and the second waveguide is formed on the photodetector side with respect to the first waveguide.

3. The OCT system according to claim 1,
wherein a first attachment being the reference attachment attached to the OCT optical system is replaced with a second attachment being the reference attachment having a different optical path length of the third waveguide from the first attachment to change the optical path length of the reference optical path.

4. The OCT system according to claim 1,
wherein a change in the optical path length of the reference light caused by attaching and detaching the reference attachment corresponds to a change in the optical path length by inserting and removing a third attachment on the measurement optical path.

5. The OCT system according to claim 1,
wherein the reference attachment includes a device that controls to vary an optical path length of the third waveguide.

6. A reference attachment configured to be attached to and detached from an OCT optical system comprising:
wherein the OCT optical system includes, a beam splitter for splitting light from an OCT light source into a measurement optical path and a reference optical path, a photodetector for detecting a spectral interference signal between measurement light guided onto tissue of a subject eye via the measurement optical path and reference light from the reference optical path, a first waveguide which forms a part of the reference optical path and is on the beam splitter side, and a second waveguide which forms a part of the reference optical path and is on the photodetector side with respect to the first waveguide, and
wherein the reference attachment includes a third waveguide and is configured to be attachable to and detachable from the OCT optical system such that the third waveguide is inserted and removed between an end portion of the first waveguide and an end portion of the second waveguide.

7. The reference attachment according to claim 6,
wherein the third waveguide is diverged to at least two of a first divergence optical path and a second divergence optical path having different optical path lengths, and reference light passing through the first divergence optical path and reference light passing through the second divergence optical path are guided to the detector simultaneously or selectively.

8. The reference attachment according to claim 7,
wherein the reference attachment includes a device that controls to vary an optical path length of the third waveguide.

* * * * *

UNITED STATES PATENT AND TRADEMARK OFFICE
CERTIFICATE OF CORRECTION

PATENT NO. : 11,291,365 B2  
APPLICATION NO. : 16/778074  
DATED : April 5, 2022  
INVENTOR(S) : Shinya Iwata, Kenji Aoki and Takuya Matsumoto Page 1 of 1

It is certified that error appears in the above-identified patent and that said Letters Patent is hereby corrected as shown below:

On the Title Page

(73) Assignee; Please delete "NTDEK CO., LTD., Aichi (JP)" and replace with -- NIDEK CO., LTD., Aichi (JP) --

Signed and Sealed this  
Twenty-eighth Day of June, 2022

Katherine Kelly Vidal  
*Director of the United States Patent and Trademark Office*